(12) United States Patent
Nallathambi et al.

(10) Patent No.: US 9,642,549 B2
(45) Date of Patent: May 9, 2017

(54) INTEGRATE AND FIRE PULSE TRAIN AUTOMATION FOR QRS DETECTION

(71) Applicant: University of Florida Research Foundation, Inc., Gainesville, FL (US)

(72) Inventors: Gabriel Nallathambi, Gainesville, FL (US); Jose C. Principe, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 14/534,442

(22) Filed: Nov. 6, 2014

(65) Prior Publication Data

US 2015/0141857 A1    May 21, 2015

Related U.S. Application Data

(60) Provisional application No. 61/906,079, filed on Nov. 19, 2013.

(51) Int. Cl.
*A61B 5/0452*    (2006.01)

(52) U.S. Cl.
CPC .................. *A61B 5/0452* (2013.01)

(58) Field of Classification Search
CPC ................................... A61B 5/0452
See application file for complete search history.

(56) References Cited

U.S. PATENT DOCUMENTS

| | | | |
|---|---|---|---|
| 5,251,626 A | 10/1993 | Nickolls et al. | |
| 5,524,631 A | 6/1996 | Zahorian et al. | |
| 5,560,370 A | 10/1996 | Verrier et al. | |
| 6,240,313 B1 | 5/2001 | Esler | |
| 6,262,678 B1 | 7/2001 | Sarpeshkar | |
| 7,336,210 B2 | 2/2008 | Lazar | |
| 8,139,654 B2 | 3/2012 | Chen et al. | |
| 2011/0282227 A1 | 11/2011 | Zhang | |
| 2013/0289426 A1* | 10/2013 | Lakshminarayan . | A61B 5/0452 600/515 |

OTHER PUBLICATIONS

Rastogi et al., Integrate and Fire Circuit as an ADC replacement, IEEE International Symposium of Circuits and Systems (ISCAS), May 2011.

* cited by examiner

*Primary Examiner* — Rex R Holmes
(74) *Attorney, Agent, or Firm* — Thomas | Horstemeyer LLP; Christopher B. Linder; Randy R. Schoen

(57) ABSTRACT

Various examples are provided for automation of QRS detection. In one example, among others, a system includes an integrate and fire (IF) sampler that can generate an IF pulse train from an analog input signal, and decision logic circuitry that can determine whether a QRS complex waveform is present in a pulse segment of the IF pulse train. In another example, a method includes generating an integrate and fire (IF) pulse train from an analog input signal, identifying a pulse segment of the IF pulse train, and determining whether a QRS waveform is present in the pulse segment based at least in part upon attributes associated with the pulse segment.

20 Claims, 11 Drawing Sheets

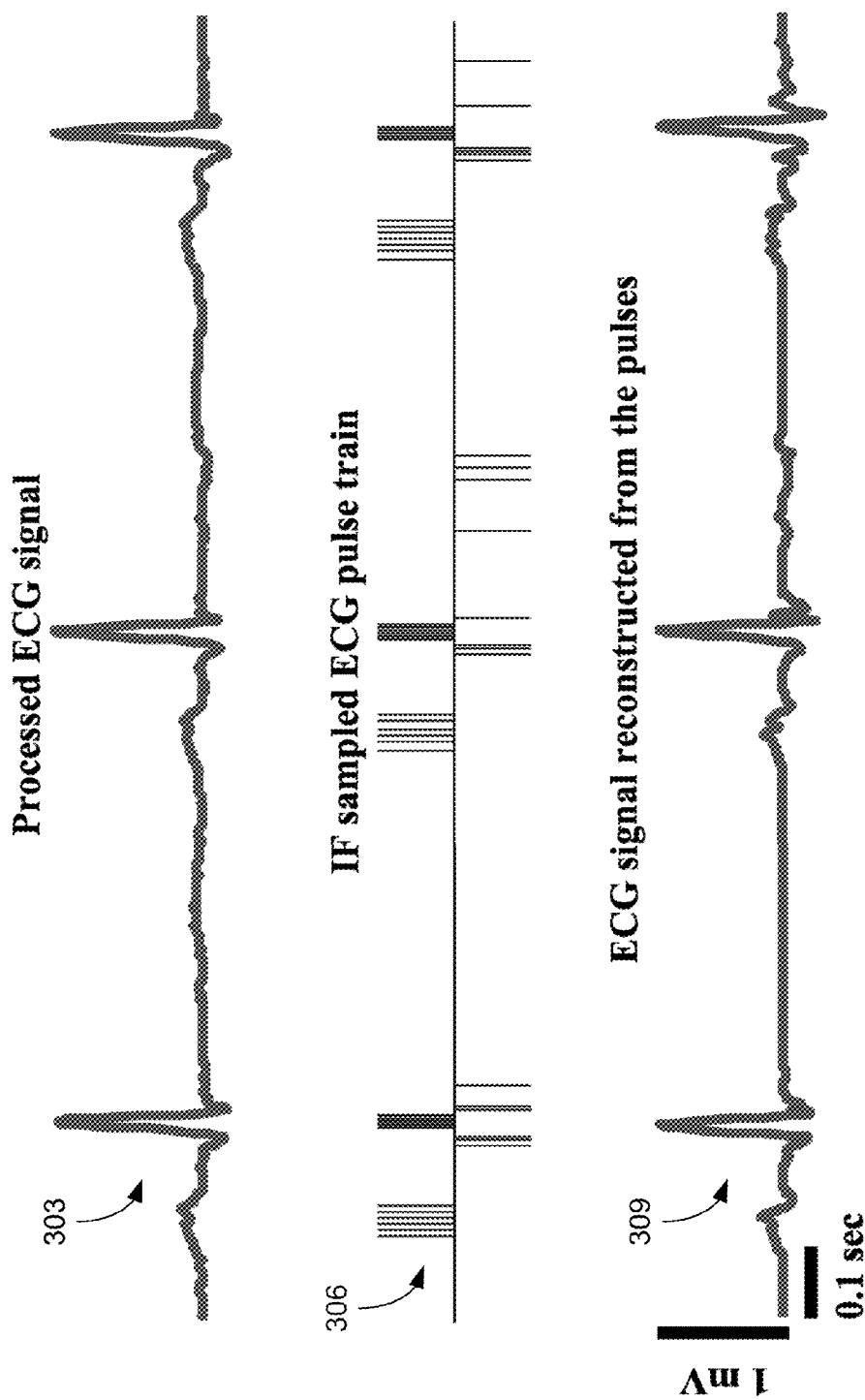

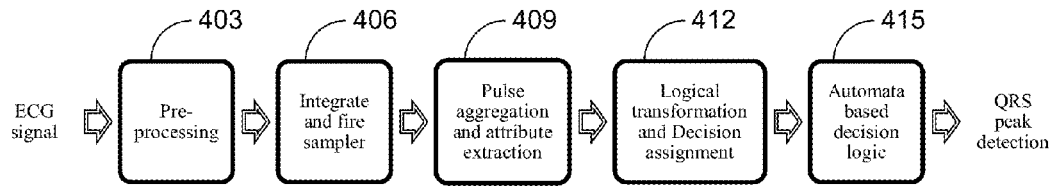

FIG. 4

DEFINITION OF PARAMETERS

| Parameter | Quantity | Detection threshold | Threshold value |
|---|---|---|---|
| *Morphological checking descriptors* | | | |
| $C_1, C_2$ | Rate descriptors | $n_1, n_2$ | Depends on IF |
| $D_1, D_2$ | Duration descriptors | $t_{d1}, t_{d2}$ | $t_{d1}=120$ms, $t_{d2}=20$ms |
| $P_1, P_2, P_3$ | Slope descriptors | $t_{p1}, t_{p2}, t_{p3}$ | Depends on IF |
| *Blanking descriptors and markers* | | | |
| $B_1, B_2$ | Strong stimulus descriptors | $c^{QRS}, m^{QRS}$ | Depends on previous QRS |
| – | Blanking markers | $t_{Bref}, t_{Sref}$ | $t_{Bref}=350$ms, $t_{Sref}=250$ms |
| *Search back discriminators and markers* | | | |
| $N_{PS}$ | Segment marker | $n$ | 7 segments |
| $D_{PS}$ | Duration discriminator | $t_{PS}$ | 1s |
| $C_{PS}$ | Rate discriminator | $n_1$ | Depends on IF |

FIG. 5

Performance Results Of QRS Detection Scheme

| Record | Total (beats) | FP (beats) | FN (beats) | FP+FN (beats) | Error (%) |
|---|---|---|---|---|---|
| 100 | 2273 | 0 | 0 | 0 | 0 |
| 101 | 1865 | 2 | 0 | 2 | 0.11 |
| 102 | 2187 | 0 | 0 | 0 | 0 |
| 103 | 2084 | 1 | 0 | 1 | 0.05 |
| 104 | 2229 | 21 | 9 | 30 | 1.34 |
| 105 | 2572 | 104 | 16 | 120 | 4.67 |
| 106 | 2027 | 61 | 2 | 63 | 3.1 |
| 107 | 2137 | 20 | 0 | 20 | 0.94 |
| 108 | 1763 | 7 | 42 | 49 | 2.78 |
| 109 | 2532 | 7 | 0 | 7 | 0.28 |
| 111 | 2124 | 5 | 7 | 12 | 0.56 |
| 112 | 2539 | 0 | 0 | 0 | 0 |
| 113 | 1795 | 0 | 0 | 0 | 0 |
| 114 | 1879 | 0 | 3 | 3 | 0.16 |
| 115 | 1953 | 0 | 0 | 0 | 0 |
| 116 | 2412 | 3 | 20 | 23 | 0.95 |
| 117 | 1535 | 0 | 0 | 0 | 0 |
| 118 | 2278 | 23 | 4 | 27 | 1.18 |
| 119 | 1987 | 6 | 0 | 6 | 0.3 |
| 121 | 1863 | 0 | 2 | 2 | 0.11 |
| 122 | 2476 | 2 | 0 | 2 | 0.08 |
| 123 | 1518 | 2 | 0 | 2 | 0.13 |
| 124 | 1619 | 24 | 0 | 24 | 1.48 |
| 200 | 2601 | 27 | 5 | 32 | 1.23 |
| 201 | 1963 | 1 | 22 | 23 | 1.17 |
| 202 | 2136 | 3 | 4 | 7 | 0.33 |
| 203 | 2980 | 37 | 92 | 129 | 4.33 |
| 205 | 2656 | 0 | 6 | 6 | 0.23 |
| 207 | 1860 | 4 | 11 | 15 | 0.81 |
| 208 | 2955 | 8 | 30 | 38 | 1.29 |
| 209 | 3005 | 4 | 1 | 5 | 0.17 |
| 210 | 2650 | 7 | 56 | 63 | 2.38 |
| 212 | 2748 | 8 | 1 | 9 | 0.33 |
| 213 | 3251 | 43 | 3 | 46 | 1.41 |
| 214 | 2262 | 4 | 2 | 6 | 0.27 |
| 215 | 3363 | 0 | 2 | 2 | 0.06 |
| 217 | 2208 | 1 | 2 | 3 | 0.14 |
| 219 | 2154 | 2 | 2 | 4 | 0.19 |
| 220 | 2048 | 1 | 0 | 1 | 0.05 |
| 221 | 2427 | 0 | 0 | 0 | 0 |
| 222 | 2483 | 1 | 79 | 80 | 3.22 |
| 223 | 2605 | 2 | 5 | 7 | 0.27 |
| 228 | 2053 | 13 | 10 | 23 | 1.12 |
| 230 | 2256 | 5 | 0 | 5 | 0.22 |
| 231 | 1571 | 26 | 1 | 27 | 1.72 |
| 232 | 1780 | 3 | 4 | 7 | 0.39 |
| 233 | 3079 | 6 | 17 | 23 | 0.75 |
| 234 | 2753 | 1 | 2 | 3 | 0.11 |
| 48 records | 109494 | 495 | 462 | 957 | 0.87 |

FIG. 9

INTEGRATE AND FIRE PULSE TRAIN AUTOMATION FOR QRS DETECTION

CROSS REFERENCE TO RELATED APPLICATIONS

This application claims priority to, and the benefit of, co-pending U.S. provisional application Ser. No. 61/906,079, entitled "INTEGRATE AND FIRE PULSE TRAIN AUTOMATON FOR QRS DETECTION" and filed on Nov. 19, 2013, which is hereby incorporated by reference in its entirety.

BACKGROUND

Cardiovascular disease (CVD) is the leading cause of death in the world and, according to the World Health Organization (WHO), an estimated 17.3 million people died from CVDs in 2008, representing 30% of all global deaths. It is predicted that by 2030, almost 23.6 million people will die from CVDs. Although a large proportion of CVDs are preventable, the chance for survival drops 10 percent per minute without defibrillation, and 639nine out of ten victims die. The electrocardiogram (ECG) is a standard tool that can be used to monitor heart function. Regular and continuous monitoring of ECG can provide the backbone for detection of fatal cardiovascular signs, timely intervention and treatment.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3 is an example of the generation of an IF pulse train with the IF sampler of FIG. 2 in accordance with various embodiments of the present disclosure.

FIG. 4 is a block diagram illustrating an example of a QRS detection scheme in accordance with various embodiments of the present disclosure.

FIG. 5 is a table of parameters associated with the QRS detection scheme of FIG. 4 in accordance with various embodiments of the present disclosure.

FIG. 9 is a table of results associated with the QRS detection scheme of FIGS. 4 and 6 in accordance with various embodiments of the present disclosure.

DETAILED DESCRIPTION

Figure 1:
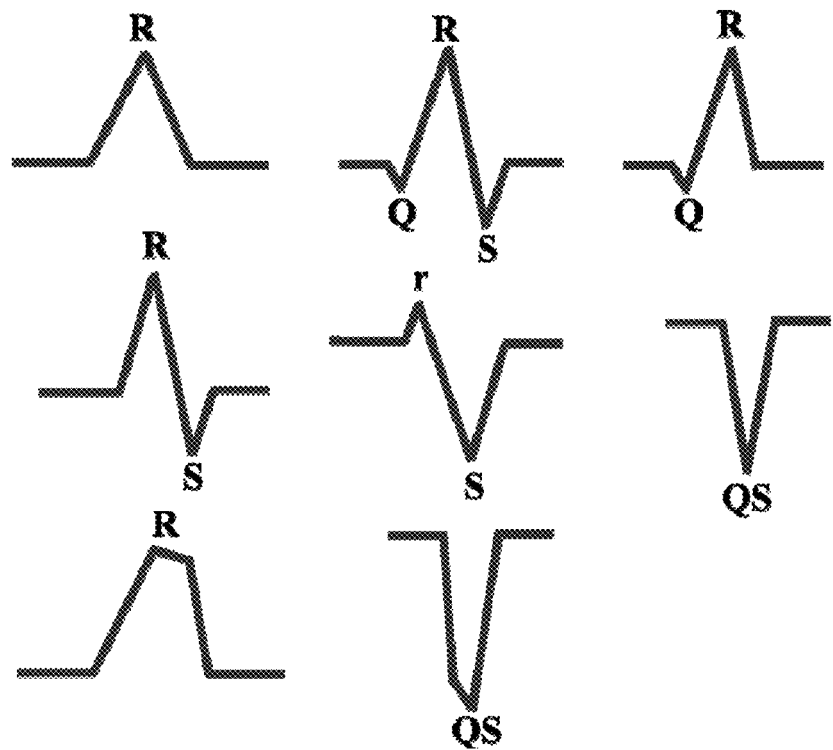
FIG. 1 is a graphical representation of examples of QRS complexes in accordance with various embodiments of the present disclosure.

Disclosed herein are various examples related to integrate and fire pulse train automation for, e.g., QRS detection in electrocardiogram (ECG) signals. Reference will now be made in detail to the description of the embodiments as illustrated in the drawings, wherein like reference numbers indicate like parts throughout the several views.

The evolution of continuous ambulatory cardiac monitoring began with the clinical use of Holter monitors in early 1960. Since then, cardiac monitoring has advanced to include features such as event monitors, atrial fibrillation (AF) auto trigger monitors and loop recorders with expanded memory and also automatic abnormal event detection arrhythmic events. Wireless technology in conjunction with a body area network (WBAN), which employs a number of physiological sensors, may be used for mobile, continuous monitoring. Unlike Holter monitors, in which the processing is done offline, WBAN systems have real time monitoring and diagnostic capabilities. WBAN systems may be broadly grouped under two categories. The first group includes wired sensors that connect to a wireless transmitter, requiring bulky equipment and hence cannot be used for continuous mobile monitoring. The second group includes an integrated wireless sensor with transmitter and hence it is a suitable candidate for continuous mobile monitoring of the patient's vital signs.

The use of processing circuitry including digital signal processing chips provides the power and flexibility to implement algorithms for signal detection. For a digital signal processing solution, the first step is to sample the data uniformly at the Nyquist rate. Signal processors use analog-to-digital converters (ADC) to represent a given signal using uniform sampling, which relies on a worst case condition (Nyquist criterion) to represent a bandlimited signal. However, this type of redundant sampling is not efficient in applications where only specific regions are of interest. For example, in biomedical signals such as ECG, the regions of interest are P, Q, R, S and T waves only.

In a typical cardiac cycle (heartbeat), the ECG comprises a P wave, a QRS complex and a T wave. The QRS complex waveform within the ECG is a reflection of the electrical activity of the heart during ventricular depolarization. Information about the time of occurrence of the QRS complex and its characteristic shape can serve as the basis of accurate automated ECG monitoring and diagnostic systems. During normal beating of the heart (sinus rhythm), the QRS complex is composed of three waves namely the Q, R and S waves over a specific period of time with specific relative size whereas during ectopic beats (e.g., ventricular rhythms) the specificity of this configuration is altered. Referring to FIG. 1, shown are examples of the most common configurations of QRS complexes encountered in practice.

In analog ECG systems, computational load and complexity influence the algorithms for hardware QRS detectors. In digital ECG systems, signal derivatives and digital filters can be used to form feature signals by separating the frequency components of a QRS complex from other signal components by comparing the feature signals against fixed or adaptive thresholds. The feature detection phase can be challenging because of noise events in the signal. The input dependent samplers concentrate on the high amplitude regions of interest in the signal and under-represent the relatively lower amplitude noisy background, thereby reducing the overall bandwidth to a sub-Nyquist rate. For instance, a set of event vectors and decision rules can be generated by filtering and used on the event vectors to discriminate QRS events from noise events. Software based approaches include wavelet transforms, genetic algorithms with optimal polynomial filters, and heuristic methods based on zero crossing counts. Wavelet transform based approaches can employ either singularity detection or filter for QRS peak detection. However, these techniques were not developed with low power constraints and can require significant computing power.

The use of redundant sampling also leads to bulky circuits with large consumption of power. Moreover, the exclusive use of DSP chips can be inefficient because only a very small fraction of its electronics is used at a given time. The use or ultra low power devices can reduce power consumption, thereby extending the operational time and battery life. In addition, sampling schemes such as compressive sensing and finite rate of innovation may be used to mitigate bulkier circuits. These sampling schemes work directly on the sparse representations of the input information and merge the compression and sampling stages reducing greatly the required data rates for reconstruction. But these methods are not designed with low power hardware constraints and hence may not be suitable for ultra low power body sensors.

To satisfy the ultra low power constraints, time based analog to pulse converters such as, e.g., integrate and fire (IF) sampling can be utilized. This pulse representation is as precise as conventional analog-to-digital conversion because it provides an injective mapping between analog signals and the pulses. For this reason, IF samplers provide an alternative to conventional Nyquist samplers. IF sampling can be applied in neural recording and ECG applications. It also has an efficient hardware implementation with a tiny form factor. Thus, IF samplers can fulfill the constraints of wearable/mobile healthcare systems such as low power, area, bandwidth and resolution.

IF sampling encodes a signal in a series of time events rather than as uniformly spaced amplitude values and therefore enables a totally different approach of data analysis that may circumvent the DSP power consumption bottleneck. For example, the pulses can be converted into integers by counting in a time interval (binning) and classifying the beats into various classes with high accuracy. IF sampling offers an advantage by providing a one to one mapping with a unique inverse. However, the binning operation may decrease the temporal resolution of the pulse train and may still utilize a DSP chip.

This disclosure presents an IF sampling scheme that quantifies the time structure of the pulses and can be fully implemented in dedicated combinatory logic, potentially decreasing the power consumption by two orders of magnitude versus DSPs. The IF sampling scheme builds a set of attributes using finite state automata to map a pulse train into ECG morphological elements using combinatory logic decision blocks, which can be accomplished without the use of DSPs. Unlike the local descriptors such as zero crossing, peak, and slope used in quantification algorithms that are very sensitive to noise, the ECG descriptors are obtained directly from the pulses. The signal variability that remains is accommodated with the proposed attributes and decision logic used in the combinatorial implementation. Thus, the IF sampling scheme is a departure from the signal processing approach based on numbers, that is enabled by the injective mapping characteristics of the IF sampling. There is practically no loss of information with ultra low power consumption. This IF sampling scheme provides a better trade-off between power and accuracy when compared with similar automated ECG systems. As is demonstrated, the preliminary results from the IF sampling scheme are comparable to state of the art techniques, but can be implemented in a fraction of the power consumption of current systems.

The IF model is inspired by a simplified biological neuron operation from computational neuroscience. Time encoding models based on IF can be based upon discrete, continuous time asynchronous sigma-delta modulators. The IF model can be considered a sampler with its output codifying the variation of the integral of the signal. Information in an IF encoded signal is in the timing between events referred to as pulses.

Figure 2:
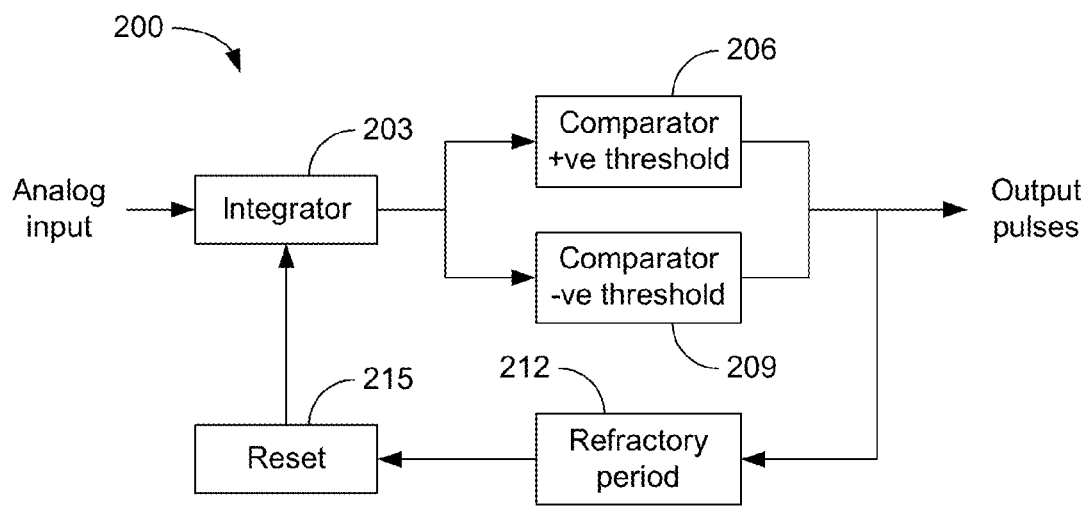
FIG. 2 is a graphical representation of an integrate and fire (IF) sampler in accordance with various embodiments of the present disclosure.

Referring now to FIG. 2, shown is a graphical representation of an example of an IF sampler 200. A continuous input x(t) is convolved with an averaging function u(t) from a starting time $t_0$ and the result is compared against pre-defined positive and negative thresholds $\{\theta_p, \theta_n\}$. When either of these thresholds is reached and/or exceeded, a pulse corresponding to the polarity of the crossed threshold is generated at that time instant representing that the input signal reached the threshold value. As shown in FIG. 2, the IF sampler 200 includes an integrator 203, comparators 206 and 209, a refractory timer 212 and a reset 215. The simplicity of the hardware circuitry of the IF sampler 200 makes it a perfect candidate for low power applications like body sensors. As the analog input x(t) is integrated, the output of the integrator 203 is compared with the two predefined thresholds $\{\theta_p, \theta_n\}$. In response to the comparison with the predefined positive and negative thresholds, a corresponding output pulse is generated by the appropriate comparator 206 or 209. The integrator 203 is reset and held at this state for a specific duration given by a defined refractory period 'τ' to prevent two pulses from being too close to each other. After the refractory period has expired, the IF sampler 200 repeats the process.

For example, let $u(t)=e^{\alpha(t-t_{k+1})}$ be the leaky factor in the integration and $t_0$ be the starting time of the continuous input signal x(t), then:

$$\theta_k = \int_{t_{k+\tau}}^{t_{k+1}} x(t)e^{\alpha(t-t_{k+1})}dt \qquad (1)$$

where $\theta_k=\{\theta_p, \theta_n\}$ and $\alpha,\tau>0$. IF sampling provides both linear constraints on the input (similar to an ADC) and constraints on the variation of the integral between samples. A non-uniformly distributed set of events is generated by this process, which can be referred to as a pulse train. The pulse train generated by IF represents the amplitude of the real world analog signal through an injective mapping, with a unique inverse between the two representations. This allows for reconstruction of the signal from the IF pulse train.

Referring to FIG. 3, shown is an example illustrating the generation of an IF pulse train. Shown at the top of FIG. 3 is a short segment of a typical ECG signal 303 with a normal sinus rhythm. The corresponding IF pulse train 306 generated by the IF sampler 200 and a ECG signal 309 reconstructed from the IF pulse train 306 are shown below the ECG signal 303. As expected, the pulses are localized in the cardiac cycle of the ECG 303. In the reconstructed ECG signal 309, the regions of interest are represented whereas the isoelectric deviations in the baseline are not represented.

The output pulses from the IF sampler cannot be easily represented using standard vector spaces prevalent in signal processing, which may be considered a disadvantage for digital signal processing methods. However, pulse train representations such as stochastic point process models, projections into reproducing kernel Hilbert spaces, linear filtering and time embeddings based on the inter pulse intervals have been used in the computational neuroscience. A different approach for pulse train processing is discussed here. Since the information in the pulse domain is contained in the timing between pulses, the extraction of information is done on the time structure of the pulse trains.

The bipolar pulses generated by IF sampler 200 are with positive or negative polarity and hence have digital amplitude (−1/+1). So the IF pulse trains are digital sequences and the theory of finite state automata and formal grammars can be applied augmented with duration constraints that have the power to perform real time recognition of the symbolic descriptors of the ECG waveform. This method of extracting information from signals is called Syntactic Pattern Recognition and provides a structured signal representation that avoids the vector space formulation so common in statistical pattern recognition. The IF pulse train is quantified in terms of attributes extracted from the pulse train. This method is a hybrid technique that combines both syntactic and statistical approaches and incorporates language syntax and contextual semantics.

Referring now to FIG. 4, shown is a block diagram illustrating an example of a QRS detection process. Beginning with 403, an ECG signal is preprocessed and, at 406, the preprocessed ECG signal (e.g., 303 of FIG. 3) is converted into a train of pulses (e.g., 306 of FIG. 3) using the IF sampler 200 (FIG. 2). At 409, the IF pulse train is aggregated on-line into different pulse segments and each segment is represented by a set of attributes which serve as descriptors of the pulse train. The decision logic can be based on, e.g., morphological checking. The attributes of the pulse segment are transformed into a set of logical values at 412. Based on the logical values, different automata based decision rules are executed at 415 and the QRS complexes are detected. The process will be discussed in more detail using the parameters defined in the table of FIG. 5. The parameters are grouped under: (1) descriptors, which describe the morphological conditions; (2) markers, which initiate a decision rule and (3) discriminators, which discriminate against noise and isoelectric deviations. Examples of threshold values are also provided in the table of FIG. 5.

Figure 6:
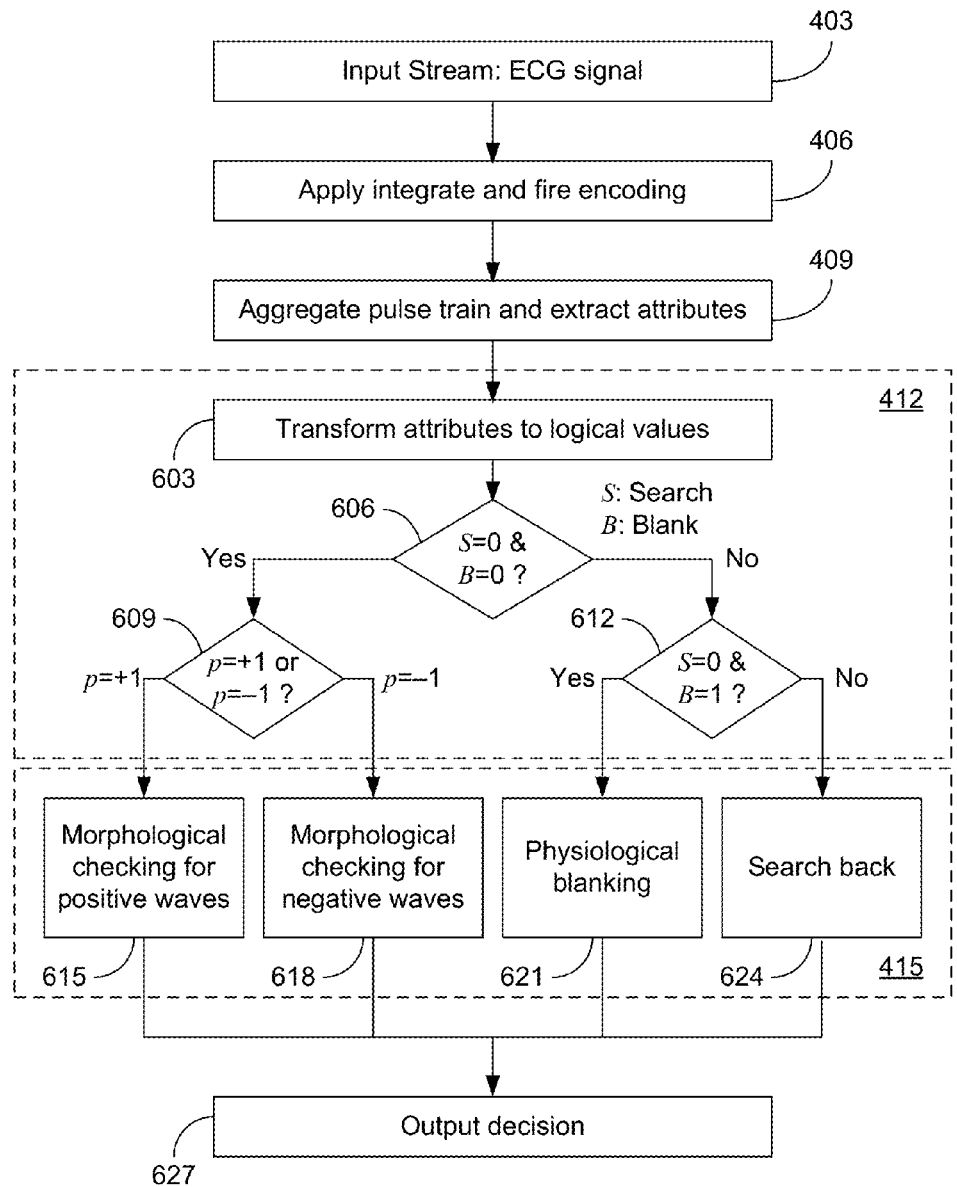
FIG. 6 is a flowchart illustrating an example of the QRS detection scheme of FIG. 4 in accordance with various embodiments of the present disclosure.

Referring to FIG. 6, shown is a flowchart illustrating an example of the QRS detection process of FIG. 4. Beginning with 403, an input stream including an analog input signal such as, e.g., an ECG signal is received. The input signal can be preprocessed to attenuate various artifacts such as, e.g., power line interference, movement and motion artifacts, electromyographic noise and baseline drift. At 406, integrate and fire encoding is applied to the input signal using IF sampling as previously described. For example, the IF sampler of FIG. 2 can be used to generate an IF pulse train for the input signal. The IF pulse train can then be aggregated at 409 to identify pulse segments and attributes for the pulse segments extracted based upon the aggregation information. To quantify the IF pulse train of an ECG signal, pulse segments are determined for the pulse train where each pulse segment is aggregated in 409 by pulses of the same polarity with an inter-pulse interval (IPI) being less than a pre-determined value $t_p$. The pulse segments of positive and negative polarity represent positive and negative waves of the ECG signal respectively and the choice of $t_p$ governs the separation of consecutive waves with the same polarity into different pulse segments. The pulse segments of interest are the QRS pulse segments in order to find the peak of the pulse segment with the maximum slope among the Q, R and S pulse segments.

Figure 7:
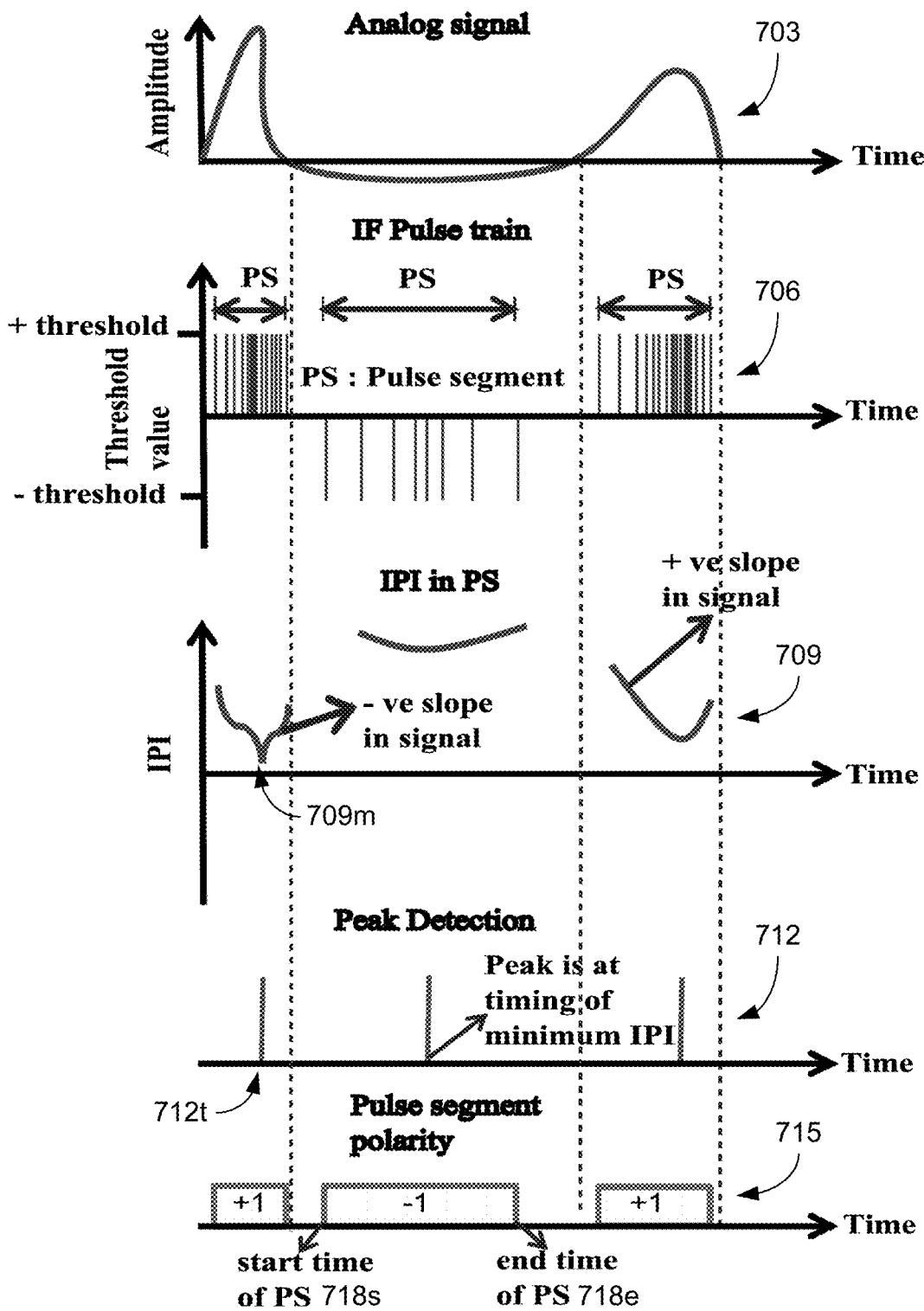
FIG. 7 is an example of pulse aggregation and extraction of attributes from an IF pulse train of the QRS detection scheme of FIGS. 4 and 6 in accordance with various embodiments of the present disclosure.

To define the time structure of the pulse segment, a set of attributes for each pulse segment can be determined in 409 from the pulse train with logic operations. The determination can be online and without using derivatives or zero crossings, which can be very noisy. FIG. 7 provides a high level illustration of an example of pulse aggregation and extraction of attributes from an IF pulse train. FIG. 7 includes an analog input signal 703 (e.g., an ECG) and a corresponding IF pulse train 706. Since information in the pulse domain is contained in the timing between pulses, the evolution of the IPI 709 over time within each pulse segment (PS) can be used to specify the slope of the signal, without taking derivatives. The time 712$t$ of the peak amplitude 712 of waves in the pulse segments can also be obtained from the IPI 709 since changes in the slope of the wave produces a corresponding change in the IPI 709 in the pulse domain. Hence, the time 712$t$ corresponding to the minimum value 709$m$ of the IPI 709 of the pulse segment corresponds to the time 712$t$ of the peak amplitude of the wave. As the output pulses of the IF sampler are tuned to the variation of the integral of the input signal 703, the energy of the signal 703 is proportional to the number of pulses in the pulse segment over time.

As illustrated in FIG. 7, an analog ECG input x(t) 703 is integrated and compared with predefined thresholds to generate the corresponding IF pulse train 706 as previously discussed. Pulse segments (PS) of the IF pulse train 706 are aggregated based upon pulses of the same polarity with an inter-pulse interval (IPI) that is less than the pre-determined value $t_p$. The pulse segments have a pulse segment polarity 715 and a start time 718$s$ and an end time 718$e$ based upon the aggregated pulses. The IF pulse train 706 of an ECG signal 703 can be encoded using attributed pulse segments, with each pulse segment having an associated attribute vector, $X_p = (p, c, t_s, t_e, m, t_m)$, where p is the polarity 715 of the pulse segment, c is the number of pulses in the pulse segment, $t_s$ and $t_e$ denote the start time 718$s$ and end time 718$e$ of the pulse segment (respectively) relative to the end time of previous R wave, m is the minimum IPI value 709$m$ of the pulse segment and $t_m$ is the time 712$t$ corresponding to the minimum IPI value 709$m$ of the pulse segment.

To quantify the morphological structure of ECG waves in signal 703, the attributes of each pulse segment can be compared against detection thresholds (see, e.g., FIG. 5) and converted to logical values at 412 of FIGS. 4 and 6. The conversion captures information from various morphological configurations of the QRS waves and the logical values serve as indicators of certain morphological conditions. In the flowchart of FIG. 6, the attributes are transformed to logical values at 603. The logical transformation can include: (1) morphological checking, where the morphological descriptors are transformed; (2) physiological blanking, where blanking descriptors are transformed to indicate strong stimulus; and (3) search back, where discriminators and the search back markers are transformed.

Morphological checking can comprise a multi-level transformation scheme to account for the morphological conditions of the ECG signal 703 (FIG. 7) under different heart rhythms. In an IF sampled ECG signal, because the slope is encoded in the IPI 709 (FIG. 7) of the pulse segments, comparison of the minimum IPI value 709*m* (FIG. 7) of a pulse segment against a detection threshold may be suffice to determine whether it is a QRS pulse segment or not.

However, with the natural variability of heart rhythms, comparison against a single detection threshold may miss QRS complexes with long durations and relatively lower slopes. For instance, during normal sinus rhythms the R waves are narrow (e.g., about 120 ms) with a high amplitude (e.g., >1 mV), whereas during abnormalities they are of extremely small duration (e.g., about 20 ms) with lower amplitude (e.g., about 0.5 mV-1 mV). Moreover, during some premature ventricular rhythms, the slope of the S wave can be relatively high when compared with the slope of other waves. In order to avoid these problems, multi-level thresholds can be used by taking into consideration the effect of morphological variations on pulse segment descriptors such as count, duration and IPI. The logical transformation of the attributes of current pulse segment can be defined as follows:

$$C_1 = c > n_1; \ C_2 = C > n_2, \quad (2)$$

$$D_1 = (t_e - t_s) > t_{d1}; \ D_2 = (t_e - t_s) > t_{d2}, \text{ and} \quad (3)$$

$$P_1 = m \le t_{p1}; \ P_2 = t_{p1} < m \le t_{p2}; \ P_3 = t_{p2} < m \le t_{p3}, \quad (4)$$

where $C_1$ and $C_2$ are rate descriptors that indicate if the number of pulses in the pulse segment exceeds thresholds $n_1$ and $n_2$ (respectively), $D_1$ and $D_2$ are duration descriptors that indicate if the pulse segment time exceeds thresholds $t_{d1}$ and $t_{d2}$ (respectively), and $P_1$, $P_2$ and $P_3$ are slope descriptors that indicate if the minimum IPI value is in a range defined by thresholds $t_{p1}$, $t_{p2}$ and $t_{p3}$.

For physiological blanking, whenever a QRS complex has been detected, there is a physiological relative refractory period with duration of about 250 ms to about 350 ms before the occurrence of the next QRS complex. However, in some rhythms like ventricular tachycardia, there is an exception to this condition when there is a strong stimulus. To account for physiological blanking, the logical transformations for strong stimulus are defined as follows:

$$B_1 = (c \le c^{QRS}) V (m \le m^{QRS}); \ B_2 = D_1 V (m \le m^{QRS}) \quad (5)$$

where $c^{QRS}$ and $m^{QRS}$ are the number of pulses and minimum IPI value in the pulse segment of the previous detected QRS wave, the symbol "V" represents a logical OR operation and $B_1$ and $B_2$ are strong stimulus descriptors with $(B_1, B_2) \in (0,1)$.

In the case of search back, to search for suspected cases of missed peaks when there is no detection for a certain period of time, the following logical transformations can be defined:

$$N_{PS} = N > n \quad (6)$$

$$D_{PS} = (t_s - t_e^{QRS}) > t_{PS} \quad (7)$$

$$G^i = \min(m_{PS}); \ C_{PS} = c^i > n_i \quad (8)$$

where N is the number of pulse segments processed until a QRS complex occurs, $t_e^{QRS}$ is the end time of the previous QRS pulse segment detected, $G^i$ is the pulse segment with the minimum IPI value amongst the other processed pulse segments after the detection of the previous QRS pulse segment with i denoting the pulse segment number after previous QRS detection, and $c^i$ denotes the number of pulses in the $i^{th}$ pulse segment. $N_{PS}$ is a segment marker, $D_{PS}$ is a duration discriminator and $C_{PS}$ is a rate discriminator with $(N_{PS}, D_{PS}, C_{PS}) \in (0,1)$.

Finally, the ECG components are assigned logical values such that:

$$QRS = R_{PS} V S_{PS} \quad (9)$$

where $R_{PS}$ and $S_{PS}$ denote the pulse segment of R and S waves, respectively, with $(QRS, R_{PS}, S_{PS}) \in (0,1)$. Logical 1 indicates detection of the corresponding wave and logical 0 indicates the wave has not been detected. Alternatively, if the both p and QRS are equal to 1, then the detected pulse segment is an R wave whereas if p=−1 (negative wave) and QRS=1, then the detected pulse segment is an S wave.

In 412 of FIGS. 4 and 6, which automata based decision logic is used can be determined based upon search and blank status and/or polarity of the pulse segment. The initiation of blanking and search back can defined as:

$$\text{Search} = \neg QRS \wedge N_{PS} \quad (10)$$

$$\text{Blank} = QRS \wedge ((t_s - t_e^R) < t_{Rref} V (t_s - t_e^S) < t_{Sref}) \quad (11)$$

where $t_e^R$ and $t_e^S$ are the end time of the previously detected R and S pulse segments respectively. The symbols "∧" and "¬" represent logical AND and negation operations, respectively. The refractory periods of varying durations are defined for R and S waves with $t_{Rref} > t_{Sref}$. Depending on the logical values of search (S) and blank (B) (i.e., 00, 01, 10), either one of four different automata can be initiated as shown in FIG. 6. Observe that by the definitions of EQNS. 10 and 11, both search and blank cannot be in logical 1 simultaneously. Also note that the morphological checking based automata have two different automatons for p=+1 (positive waves) and p=−1 (negative waves). In some embodiments, a positive wave can be indicated by p=1 and a negative wave can be indicated by p=0.

For example, after transforming the attributes to logical values in 603, logical values for search (S) and blank (B) are examined in 606. In response to both S=0 and B=0, the polarity p of the pulse segment (e.g., 715 of FIG. 7) is examined in 609. In the case of a positive wave (p=+1), then morphological checking for positive waves is carried out in 615. Where it is a negative wave (p=−1), then morphological checking for negative waves is carried out in 618. If either S≠0 or B≠0, then S and B are reexamined in 612. In response to S=0 and B=1, physiological blanking is carried out in 621. In response to S=1 and B=0, search back is carried out in 624. In this way, the appropriate automata based decision logic can be quickly determined.

In response to the determination of 412, one of the four different automata based decision rules can be executed at 415. A deterministic finite automaton (DFA) is a 5-tuple or quintuple (W, Σ, δ, $w_0$, F) including a finite set of states (W), a finite set of input symbols called the alphabet (Σ), a transition function (δ: W×Σ→W), a start state ($w_0 \in W$), and a set of accept states (F ⊆ W). The logical descriptors can be the input to the automaton and govern the transition function. The final state of the automaton determines whether the pulse segment under consideration belongs to QRS wave or not and also whether if it's to be discarded as noise. FIGS. 8A-8D shows examples of state diagrams for each of the four DFA: morphological checking for positive waves 615; morphological checking for negative waves 618; physiological blanking 621; and search back 624, respectively.

Figure 8A:
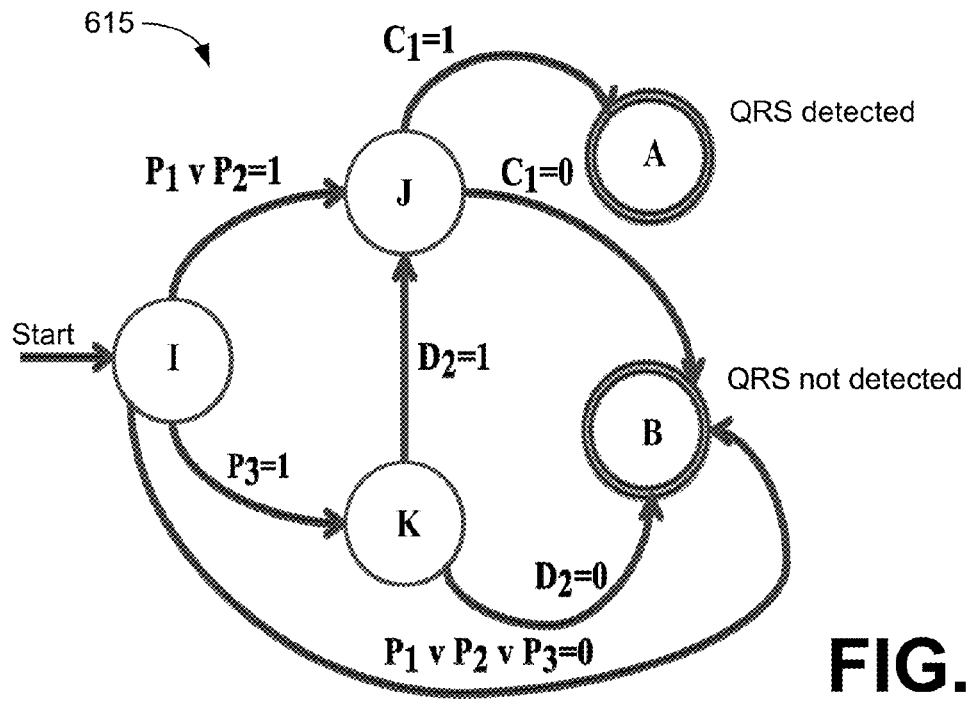
FIGS. 8A through 8D are state diagrams illustrating examples of automata based decision rules of the QRS detection scheme of FIGS. 4 and 6 in accordance with various embodiments of the present disclosure.

Referring to FIG. 8A, an example of the morphological checking DFA 615 for p=1 can be given by states W={I, J, K, A, B}, inputs E={$C_1$, $D_2$, $P_1$, $P_2$, $P_3$} as defined in the table of FIG. 5 and EQNS. 2-4, a start state of $w_0$=I and accept states F={A, B} where A denotes the detection of a QRS pulse segment and B denotes that a QRS pulse segment is not detected. The state transitions δ are chosen to account for different morphological variations of R waves and are shown in FIG. 8A. The connector and the arrow indicate the transition from one state to another until the final state is reached. The symbol "V" represents a logical OR operation. For a given pulse segment to be a QRS pulse segment, the rate descriptor $C_1$ must be at logical 1 with either one of the slope descriptors $P_1$ and $P_2$ set to logical 1 or the slope descriptor $P_3$ and the duration descriptor $D_2$ set to logical 1.

In the example of FIG. 8A, the morphological checking DFA 615 transitions from initial state I based upon the slope descriptors ($P_1$, $P_2$, $P_3$) of the pulse segment being checked. If $P_1$ V $P_2$ V $P_3$=0, the DFA 615 transitions to state B and no QRS wave is detected. Otherwise, if $P_1$ V $P_2$=1 the DFA 615 transitions to state J or if $P_3$=1 the DFA 615 transitions to state K. From state K, the morphological checking DFA 615 transitions based upon the duration descriptor ($D_2$). If $D_2$=0, the DFA 615 transitions to state B and no QRS wave is detected. If $D_2$=1, the DFA 615 transitions to stater From state J, the morphological checking DFA 615 transitions based upon the rate descriptor ($C_1$). If $C_1$=0, the DFA 615 transitions to state B and no QRS wave is detected. If $C_1$=1, the DFA 615 transitions to state A and a QRS wave is detected in that segment.

Figure 8B:
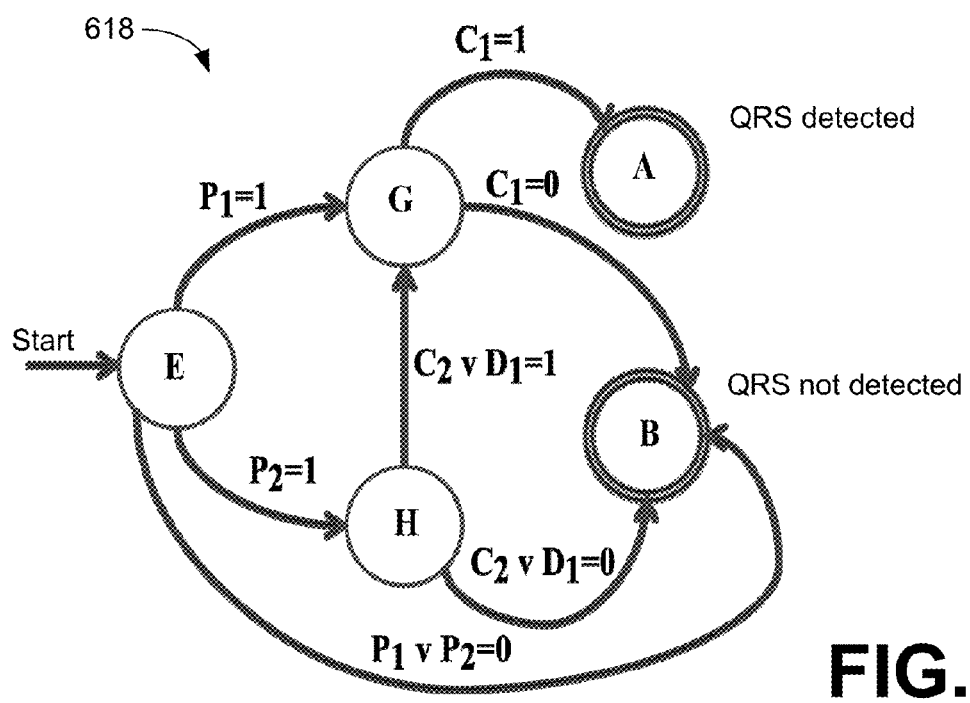

Similarly, an example of the morphological checking DFA 618 for p=−1 is shown in FIG. 8B. The DFA 618 can be given by states W={E, G, H, A, B}, inputs Σ={$C_1$, $C_2$, $D_1$, $P_1$, $P_2$} as defined in the table of FIG. 5 and EQNS. 2-4, a start state of $w_0$=E and accept states F={A, B} with the state transitions δ shown in FIG. 8B. In FIG. 8B, the morphological checking DFA 618 transitions from initial state E based upon the slope descriptors ($P_1$, $P_2$, $P_3$) of the pulse segment being checked. If $P_1$ V $P_2$=0, the DFA 618 transitions to state B and no QRS wave is detected. Otherwise, if $P_1$=1 the DFA 618 transitions to state G or if $P_2$=1 the DFA 618 transitions to state H. From state H, the morphological checking DFA 618 transitions based upon the rate descriptor ($C_2$) and the duration descriptor ($D_2$). If $C_2$ V $D_2$=0, the DFA 618 transitions to state B and no QRS wave is detected. If $C_2$ V $D_2$=1, the DFA 618 transitions to state G. From state G, the morphological checking DFA 618 transitions based upon the rate descriptor ($C_1$). If $C_1$=0, the DFA 618 transitions to state B and no QRS wave is detected. If $C_1$=1, the DFA 618 transitions to state A and a QRS wave is detected in that segment.

Figure 8C:
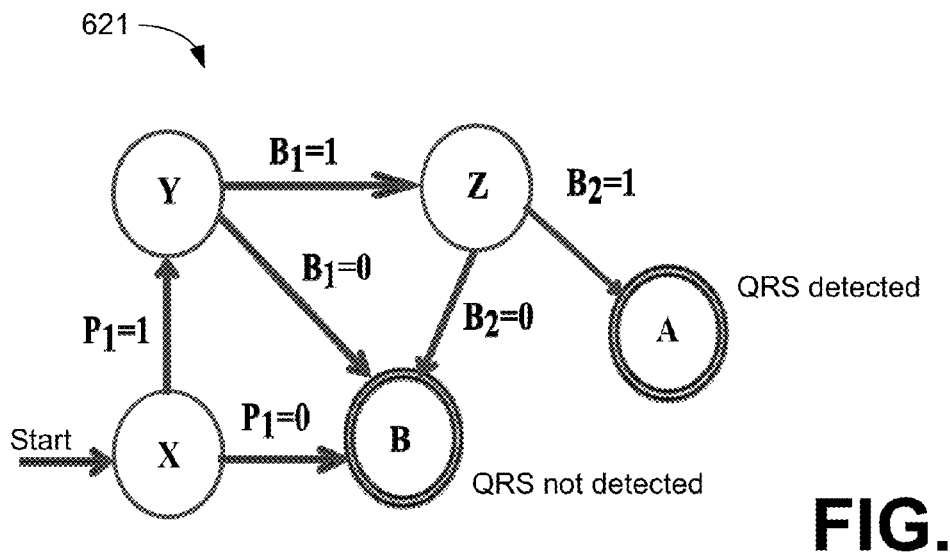

Referring now to FIG. 8C, an example of the DFA for blanking 621 can be given by states W={X, Y, Z, A, B}, inputs Ξ={$P_1$, $B_1$, $B_2$} as defined in the table of FIG. 5 and EQNS. 3-5, a start state of $w_0$=X and accept states F={A, B} with the state transitions δ shown in FIG. 8C. In FIG. 8C, the blanking DFA 621 transitions from initial state X based upon the slope descriptor ($P_1$) of the pulse segment being checked. If $P_1$=0, the DFA 621 transitions to state B and no QRS wave is detected. Otherwise, if $P_1$=1 the DFA 621 transitions to state Y. From state Y, the morphological checking DFA 621 transitions based upon the strong stimulus descriptor ($B_1$). If $B_1$=0, the DFA 621 transitions to state B and no QRS wave is detected. If $B_1$=1, the DFA 621 transitions to state Z. From state Z, the morphological checking DFA 621 transitions based upon the strong stimulus descriptor ($B_2$). If $B_2$=0, the DFA 621 transitions to state B and no QRS wave is detected. If $B_2$=1, the DFA 621 transitions to state A and a QRS wave is detected in that segment.

Figure 8D:
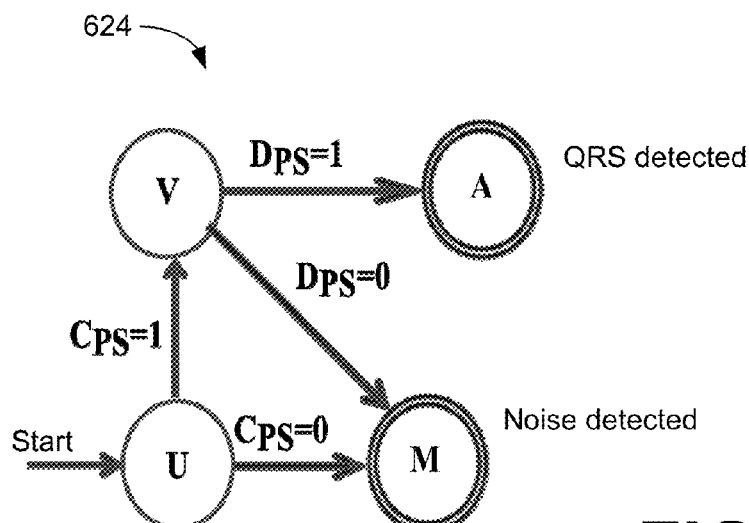

Referring next to FIG. 8D, an example of the DFA for search 624 can be given by states W={U, V, A, M}, inputs Ξ={$C_{PS}$, $D_{PS}$} as defined in the table of FIG. 5 and EQNS. 7-8, a start state of $w_0$=U and accept states F={A, M} where the state M denotes noisy pulse segments and isoelectric deviations, which are discarded as noise. The state transitions δ of the search DFA 624 are shown in FIG. 8D. In FIG. 8D, the blanking DFA 624 transitions from initial state U based upon the rate discriminator ($C_{PS}$) of the pulse segment being checked. If $C_{PS}$=0, the DFA 624 transitions to state M indicating that a noisy pulse segment is detected. Otherwise, if $C_{PS}$=1 the DFA 624 transitions to state V. From state V, the morphological checking DFA 624 transitions based upon the duration discriminator ($D_{PS}$). If $D_{PS}$=0, the DFA 624 transitions to state M indicating that a noisy pulse segment is detected. If $D_{PS}$=1, the DFA 624 transitions to state A and a QRS wave is detected in that segment.

Referring back to the flowchart of FIG. 6, an output decision is provided in 627 based upon the results of the automata based decision rules executed at 415. The output decision can indicate that a QRS pulse segment is detected, the pulse segment is not a QRS segment, or that a noisy pulse segment was detected. When a QRS pulse segment is detected, the QRS peak time 712*t* (FIG. 7) is given by $t_m$, which is the time corresponding to the minimum IPI value 709*m* (FIG. 7) of the detected pulse segment. Although an attribute grammar has been implemented, the attributes allow for the use of decision logic circuitry (e.g., flip flops and/or combinatory logic) based exclusively on relational and logical operators, for ultra fast and ultra low power implementation.

Annotated ECG databases such as MIT-BIH database, AHA database, Ann Arbor Electrogram Libraries and CSE database are available for the evaluation of QRS detection algorithms. The standard MIT-BIH arrhythmia database was used to test the performance of the proposed QRS peak detection algorithm. The database consists of 48 fully annotated, 30 minute, two-lead ECG recordings from 47 different patients (recordings 201 and 202 are from the same patient) among which twenty-five recordings (records number 200 and above) have rare arrhythmias. The leads usually involve the modified limb lead II (MLLII) and one of the modified leads V1, V2, V4 or V5. Since the second lead usually varies for each recording (patient), the results presented herein are based on the first lead. The data is sampled at 360 Hz and the ±5 mV range is quantized to 11-bits. While some records contain clear R-peaks and few artifacts (e.g., records 100-103, records 112-115), for some records the detection of QRS complexes is very difficult due to abnormal shapes, noise, and artifacts (e.g., records 105, 203, 222).

Various artifacts such as power line interference, movement and motion artifacts, electromyographic noise and baseline drift were observed in the MIT-BIH database. The recordings were pre-processed to attenuate the artifacts. Although the preprocessing was preformed using digital processing, the preprocessing allowed our results to compared with the results in the literature. The ECG signal was passed through a median filter with window size 200 ms which removes the P-waves and QRS complexes. Then a median filter with window size 600 ms, removed the T-waves. The filtered signal represents the baseline which was then subtracted from the original ECG recording. Finally a notch filter centered at 60 Hz was implemented through a 60 tap finite impulse response filter to remove power line interference.

All 48 records in MIT-BIH database were tested with the exception of ventricular flutter wave episodes in record 207. FIG. 9 provides a table that lists the record-by-record performance of the IF pulse train automation for QRS detection. The QRS detection scheme succeeded in detecting 99.13% of total peaks with sensitivity ($S_e$) and positive predictivity (+P) of 99.58% and 99.55%, respectively. The results obtained with MIT-BIH database demonstrate the ability of the QRS detection scheme to provide precise and accurate QRS detection.

Figure 10:
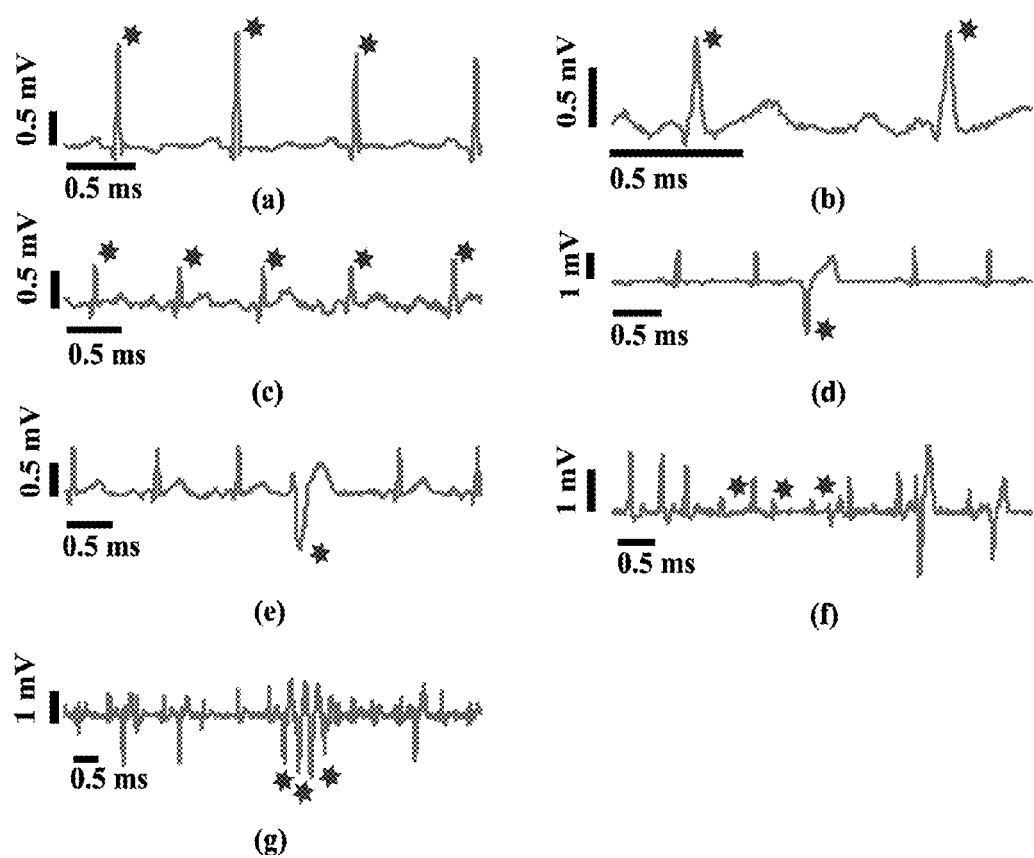
FIG. 10 is a graphical representation of examples of QRS morphologies in accordance with various embodiments of the present disclosure.

As can be understood, choice of detection thresholds directly influences the decision making. Due to wide inter and intra patient variability, traditional estimators will yield precise accuracy only in certain segments of the ECG signal. Therefore, the Minnesota ECG coding manual, which provides systematic criteria for occurrence of cardiac events, was used to fix the detection thresholds. Based on the morphological constraints for QRS detection in the pulse domain in conjunction with the lower margin of detection established by Minnesota ECG coding manual, parameters for IF sampling were determines. The data in the MIT-BIH was used for testing. FIG. 10 shows examples of different QRS morphologies from the MIT-BIH database that illustrate the amplitude slope and duration constraints. The points of interest in FIG. 10 are denoted by a star (*). FIG. 10(a) illustrates high amplitude (>1 mV), narrow (around 120 ms) R waves, FIG. 10(b) shows relatively lower amplitude (1 to 0.7 mV) R waves, and FIG. 10(c) depicts lower amplitude (0.7 to 0.5 mV) extremely narrow (around 20 ms) R waves. FIG. 10(d) illustrates high amplitude (>1 mV) S waves, FIG. 10(e) shows relatively lower amplitude (1 to 0.7 mV) S waves, and FIG. 10(f) depicts low amplitude R waves during search back. FIG. 10(g) strong stimulus during the blanking period.

The IF sampler parameters were chosen as $\theta_p = -\theta_n = 0.0008$, $\alpha = 40$, and $\tau = 1$ ms such that the smallest allowable P wave specified by Minnesota ECG coding manual is represented by at least two IPI periods. The time $t_p$ was chosen based on the minimum duration of Q and S waves such that two consecutive positive segments are segmented separately and was defined as $t_p = 60$ ms. The detection thresholds based on m and c are dependent upon the IF sampler parameters. For the given IF sampler parameters, the IF dependent thresholds in the table of FIG. 4 are given by $t_{p1} = 2$ ms, $t_{p2} = 3$ ms, and $t_{p3} = 3.5$ ms, $n_1 = 3$ and $n_2 = 19$. The physiological refractory period values are given by $t_{Rref} = 350$ ms and $t_{Sref} = 250$ ms, and the duration thresholds were given by $t_{d1} = 120$ ms and $t_{d2} = 20$ ms. The thresholds during the search back component of the algorithm were chosen as $t_{PS} = 1$s and $n = 7$ to account for one complete cardiac cycle after previous QRS detection.

The reliability of the QRS detection scheme is evaluated by detection error rate, which expresses the accuracy of the algorithm, sensitivity $S_e$, which is the ability of the algorithm to correctly detect beats, and the positive predictivity +P, which is the discriminability between true and false beats, defined as follows:

$$\text{Error} = \frac{FP + FN}{TP + FN};$$
$$S_e = \frac{TP}{TP + FN};$$
$$+P = \frac{TP}{TP + FP}$$

(12)

where TP is the number of true positives which refers to beats that are correctly detected, FN is the number of false negatives which refers to beats that are not detected, FP is the number of false positives which refers to falsely detected beats.

Figure 11:
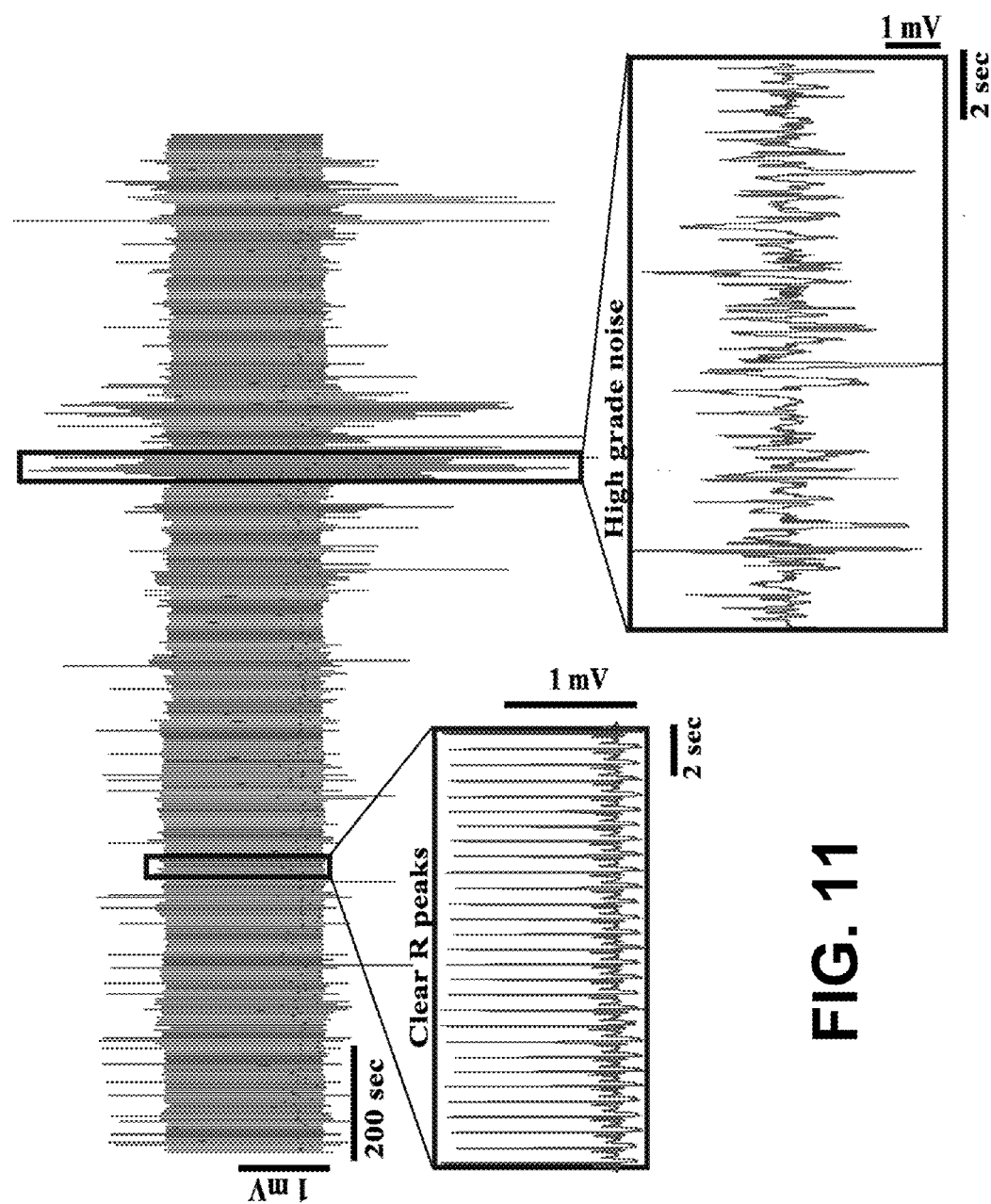
FIG. 11 illustrates the presence of high grade noise that degrades signal quality in accordance with various embodiments of the present disclosure.

Although the overall performance is good, in some records the percentage of error is relatively higher than other records. Records such as 105, 106, 203, and 222 produced relatively higher error rates. Most of the errors in these records were due to high grade noise, QRS morphology changes due to axis shifts, muscle artifact and other problems. For instance, FIG. 11 shows the high grade noise that degrades the signal quality in record 105 after the 20th minute. This noise causes the detection error rate to increase sharply from 0.95% during the first twenty minutes, where the peak of R waves are clear, to 11.62% during the last ten minutes, where the waves are completely distorted beyond expert recognition. Nevertheless, the overall results were good with the worst case error rate being 4.67%, which is reasonably low when compared with state of the art methods.

The Association for the Advancement of Medical Instrumentation (AAMI) has developed a standard for the performance of cardiac monitors known as ANSI/AAMI EC13 that addresses minimum performance standards for QRS detection in cardiac devices. The noise guidelines of EC13 standard specify that QRS detectors must tolerate line frequency voltage and drift. QRS complexes need to be reliably detected in presence of 100 µV peak-to-peak 60 Hz line frequency noise and a drift of 0.1 Hz triangular wave with 4 mV peak-to-peak amplitude. The standard also specifies that QRS complexes with widths less than 10 ms should not be detected. To satisfy this, the duration descriptors were modified to include a lower limit of 10 ms. When tested for drift and line frequency tolerance, the QRS detection scheme produced sensitivity and positive predictivity values of 99.28% and 99.37%, respectively. This demonstrates that the QRS detection scheme is robust to noise as per EC13 standard.

The QRS detection scheme is comparable to the state-of-the-art methods. Digital pre-processing was implemented to allow the results to be compared with similar state-of-the-art methods such as, e.g., H. Inoue et al. ("Detection of QRS complex in ECG using wavelet transform", IEICE Gen. Conf., vol. 67, no. A-4, p. 198, March 1997) with min[$S_e$,+P]>99% and Y. Sun et al ("Microcontroller-based real-time QRS detection," *Biomed. Instrum. Technol.*, vol. 26, no. 6, pp. 477-484, 1992) with min[$S_e$,+P] of 95%-99%. Since many of the methods are software based approaches, the QRS detection scheme can be implemented in dedicated hardware using combinatorial logic and/or flip flops, which provides a significant advantage when compared with other methods in terms of size and ultra low power. This implementation can be built with an electrode, which could offer at least two orders of magnitude less power than current DSP based algorithms.

Figure 12:
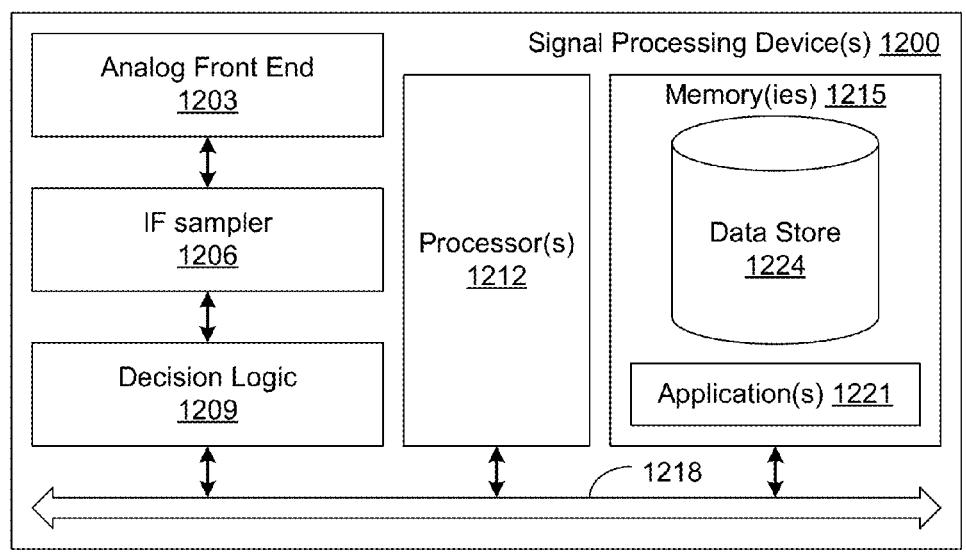
FIG. 12 is a schematic block diagram of a signal processing device in accordance with various embodiments of the present disclosure.

Referring to FIG. 12, shown is a schematic block diagram of an example of a signal processing device 1200 that can be used to implement the QRS detection scheme in accordance with various embodiments of the present disclosure. The signal processing device 1200 can include an analog front end 1203 including circuitry configured to preprocess analog signals such as, e.g., ECG signals. While digital pre-processing was utilized so that the results could be compared with similar state-of-the-art methods, pre-processing filters such as notch and median filters can be implemented as part of a low power analog front-end 1203. Ultra low power analog notch and median filters can be used for removal of power line noise and baseline wander, respectively. For instance, an adaptive zero frequency notch filter or a median filter can be used to remove baseline wander. These adaptive filters can be fabricated in continuous-time, low power analog VLSI. For example, an adaptive filter can use a least mean square (LMS) algorithm with a single weight. The accuracy of detection may be improved further by using automatic gain control. To satisfy low power constraints, a variable gain control can be provided in the pulse domain.

The signal processing device 1200 also can include an IF sampler 1206 for generating an IF pulse train from the analog signal and decision logic 1209 for implementing the QRS detection scheme on the IF pulse train. The IF sampler 1206 can include circuitry configured to implement, e.g., the IF sampler 200 of FIG. 2. The decision logic 1209 also includes circuitry that can be implemented in dedicated hardware using, e.g., combinatorial logic and/or flip flops to reduce processing speed and power consumption. For example, the decision logic 1209 can be configured to aggregate and extract attributes from the pulse train, transform the attributes to logical values, determine the appropriate automata based decision logic based upon the logical values, and/or determine whether a QRS complex wave is present in a pulse segment to implement the QRS detection scheme. The signal processing device 1200 can also include at least one processing circuit, for example, having a processor 1212 and a memory 1215, both of which are coupled to a local interface 1218. The decision logic 1209 can also be coupled to the local interface 1218. The local interface 1218 can comprise, for example, a data bus with an accompanying address/control bus or other bus structure as can be appreciated. In some embodiments, the processing circuit can implement at least a portion of the QRS detection scheme in conjunction with the decision logic 1209.

Stored in the memory 1215 can be both data and several components that are executable by the processor 1212. In particular, stored in the memory 1215 and executable by the processor 1215 can be one or more applications 1221. In some implementations, the applications can include an application for implementing a portion of the QRS detection scheme. Also stored in the memory 1215 may be a data store 1224 and other data. In addition, an operating system may be stored in the memory 1215 and executable by the processor 1212.

It is understood that there may be other applications that are stored in the memory 1215 and are executable by the processor 1212 as can be appreciated. Where any component discussed herein is implemented in the form of software, any one of a number of programming languages may be employed such as, for example, C, C++, C#, Objective C, Java®, JavaScript®, Pen, PHP, Visual Basic®, Python®, Ruby, Delphi®, Flash®, or other programming languages.

A number of software components can be stored in the memory 1215 which are executable by the processor 1212. In this respect, the term "executable" means a program file that is in a form that can ultimately be run by the processor 1212. Examples of executable programs may be, for example, a compiled program that can be translated into machine code in a format that can be loaded into a random access portion of the memory 1215 and run by the processor 1212, source code that may be expressed in proper format such as object code that is capable of being loaded into a random access portion of the memory 1215 and executed by the processor 1212, or source code that may be interpreted by another executable program to generate instructions in a random access portion of the memory 406 to be executed by the processor 1212, etc. An executable program may be stored in any portion or component of the memory 406 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1215 is defined herein as including both volatile and nonvolatile memory and data storage components. Volatile components are those that do not retain data values upon loss of power. Nonvolatile components are those that retain data upon a loss of power. Thus, the memory 1215 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1212 may represent multiple processors 1212 and the memory 1215 may represent multiple memories 1215 that operate in parallel processing circuits, respectively. In such a case, the local interface 1218 may be an appropriate network that facilitates communication between any two of the multiple processors 1212, between any processor 1212 and any of the memories 1215, or between any two of the memories 1215, etc. The local interface 1218 may also facilitate communication between the decision logic 1209 and one or more processors 1212. The processor 1212 may be of electrical or of some other available construction.

Although application(s) 1221 and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Although the flowchart of FIG. 6 shows a specific order of execution, it is understood that the order of execution may differ from that which is depicted. For example, the order of execution of two or more blocks may be scrambled relative to the order shown. Also, two or more blocks shown in succession in FIG. 6 may be executed concurrently or with partial concurrence. Further, in some embodiments, one or more of the blocks shown in FIG. 6 may be skipped or omitted (in favor, e.g., measured travel times). In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the application(s) 1221, that comprises software or code can be embodied in any non-transitory computer-readable medium for use by or in connection with an instruction execution system such as, for example, a processor 1212 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

In this disclosure, processing a pulse train generated by an IF sampler has been discussed. The IF sampling maps the analog input signal into a pulse train, with guarantees of fidelity similar to Nyquist samplers, but allows for implementation of non-numeric signal processing with a few hundred combinatory logic and flip flop blocks. This allows for ultra small and ultra low power devices that can be encapsulated with the electrodes. The morphological features extracted using the IF sampler are more discriminative because they are extracted from the pulse train structure directly. The attribute grammar implementation also creates flexibility which provides performance accuracy. ECG delineation and beat classification can also be implemented using the attribute based framework. Such pulse attribute based systems can be used for ECG signal processing and can be implemented in wireless body area networks to monitor and diagnose the physiological vital signs.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A system for QRS complex waveform detection, comprising:
    an integrate and fire (IF) sampler configured to generate an IF pulse train from an analog input signal; and
    decision logic circuitry configured to:
        identify a pulse segment based at least in part upon pulse polarities of the IF pulse train; and
        determine whether a QRS complex waveform is present in the pulse segment of the IF pulse train.

2. The system of claim 1, wherein the decision logic circuitry is configured to aggregate pulses of the IF pulse train into a plurality of pulse segments based at least in part upon the pulse polarities and an inter-pulse interval (IPI) between pulses in the plurality of pulse segments.

3. The system of claim 1, wherein the decision logic circuitry is configured to extract attributes associated with the pulse segment of the IF pulse train, the attributes comprising at least one attribute based upon an inter-pulse interval (IPI) between pulses in the pulse segment.

4. The system of claim 3, wherein the decision logic circuitry is configured to transform the attributes into logical values.

5. The system of claim 4, wherein the decision logic circuitry is configured to determine the presence of the QRS complex waveform in the pulse segment based upon at least a portion of the logical values.

6. The system of claim 1, wherein the presence of the QRS complex waveform in the pulse segment is determined using an automata based decision logic based upon attributes associated with the pulse segment.

7. The system of claim 6, wherein the automata based decision logic is selected from a group consisting of morphological checking for positive waves, morphological checking for negative waves, physiological blanking and search back.

8. The system of claim 1, comprising an analog front end configured to preprocess the analog input signal.

9. The system of claim 1, wherein the decision logic circuitry is configured to determine whether the pulse segment is noisy.

10. A method for QRS complex waveform detection, comprising:
    generating an integrate and fire (IF) pulse train from an analog input signal;
    identifying a pulse segment of the IF pulse train; and
    determining whether a QRS waveform is present in the pulse segment based at least in part upon attributes associated with the pulse segment, the attributes comprising at least one attribute based upon an inter-pulse interval (IPI) between pulses in the pulse segment.

11. The method of claim 10, wherein identifying the pulse segment comprises aggregating pulses of the IF pulse train into a plurality of pulse segments based at least in part upon pulse polarities and inter-pulse intervals (IPI).

12. The method of claim 11, wherein the aggregation is based upon pulses of the same polarity with an IPI that is less than a pre-determined value.

13. The method of claim 10, wherein the presence of the QRS waveform in the pulse segment is determined based upon logical values corresponding to the attributes associated with the pulse segment.

14. The method of claim 10, wherein the attributes are extracted from the pulse segment, the attributes comprising a minimum IPI value for the IPI in the pulse segment and a time corresponding to the minimum IPI value.

15. The method of claim 13, wherein the presence of the QRS waveform is determined using one of a plurality of automata based decision logic based at least in part upon the logical values.

16. The method of claim 15, wherein the automata based decision logic is selected from a group consisting of morphological checking for positive waves, morphological checking for negative waves, physiological blanking and search back.

17. The method of claim 15, wherein the logical values comprise search and blank status.

18. The method of claim 10, wherein determining whether the QRS waveform is present in the pulse segment comprises determining whether the pulse segment is noisy.

19. The method of claim 10, wherein the analog signal is an electrocardiogram (ECG) signal.

20. The system of claim 3, wherein the attributes comprise a minimum IPI value for the IPI in the pulse segment and a time corresponding to the minimum IPI value.

\* \* \* \* \*